United States Patent
Londo et al.

(10) Patent No.: US 8,192,698 B2
(45) Date of Patent: Jun. 5, 2012

(54) SAMPLING PROBE, GRIPPER AND INTERFACE FOR LABORATORY SAMPLE MANAGEMENT SYSTEMS

(75) Inventors: Thomas R. Londo, Ashland, MA (US);
Paul M. Grippo, Bedford, NH (US);
Frank Sylva, The Villages, FL (US)

(73) Assignee: Parker-Hannifin Corporation, Cleveland, OH (US)

( * ) Notice: Subject to any disclaimer, the term of this patent is extended or adjusted under 35 U.S.C. 154(b) by 385 days.

(21) Appl. No.: 12/338,292

(22) Filed: Dec. 18, 2008

(65) Prior Publication Data

US 2009/0158862 A1 Jun. 25, 2009

Related U.S. Application Data

(63) Continuation-in-part of application No. 11/814,987, filed as application No. PCT/US2006/002845 on Jan. 27, 2006, now Pat. No. 8,057,756.

(60) Provisional application No. 61/015,487, filed on Dec. 20, 2007.

(51) Int. Cl.
*B01L 3/02* (2006.01)
(52) U.S. Cl. .................. 422/501; 73/864.01; 73/864.24; 73/864.25; 422/500
(58) Field of Classification Search .............. 73/864, 73/864.01, 864.11, 864.13, 864.14, 864.16, 73/864.24, 864.25, 864.87; 422/500, 501, 422/509, 524, 525, 99, 100; 206/571
See application file for complete search history.

(56) References Cited

U.S. PATENT DOCUMENTS

| 2,771,217 | A | * | 11/1956 | Brown et al. | 222/43 |
| 3,279,659 | A | | 10/1966 | Harris, Jr. | |
| 3,401,692 | A | | 9/1968 | Harris, Jr. | |
| 3,498,135 | A | * | 3/1970 | Jerg et al. | 73/864.18 |
| 3,604,267 | A | * | 9/1971 | Johns | 73/864.82 |
| 3,650,306 | A | * | 3/1972 | Lancaster | 141/238 |
| 3,957,051 | A | | 5/1976 | Topham | |
| 4,106,911 | A | * | 8/1978 | Marcelli | 422/63 |
| 4,162,030 | A | | 7/1979 | Capra et al. | |
| 4,276,048 | A | * | 6/1981 | Leaback | 436/180 |
| 4,283,950 | A | * | 8/1981 | Tervamaki | 73/864.14 |

(Continued)

FOREIGN PATENT DOCUMENTS

CA 2 047 636 7/1991
(Continued)

OTHER PUBLICATIONS

Agilent Technologies, Agilent 1100 Series Injection Systems, Mar. 1, 2004, 8 pages.

(Continued)

*Primary Examiner* — David Rogers
(74) *Attorney, Agent, or Firm* — Renner, Otto, Boisselle & Sklar, LLP

(57) ABSTRACT

A self-contained sampling probe characterized by a drive module and a syringe module removably coupled coaxially to the drive module to allow for different syringe modules to be interchangeably coupled to the drive module. The coupling is effected by quick connect and disconnect devices, and the syringe module may carry an identifier. The probe is engageable by a gripper or insertable in an interface device, both of which provide for communication of the probe with other system components. The probe has a dimension that is 8 mm or less in at least one projection coincident with an aspirate/dispense axis of the probe.

8 Claims, 9 Drawing Sheets

U.S. PATENT DOCUMENTS

| | | | |
|---|---|---|---|
| 4,346,742 A | | 8/1982 | Chase et al. |
| 4,362,064 A | * | 12/1982 | Marteau d'Autry ........ 73/864.13 |
| 4,399,711 A | * | 8/1983 | Klein ........................ 73/864.16 |
| 4,444,062 A | * | 4/1984 | Bennett et al. ............. 73/863.32 |
| 4,459,864 A | * | 7/1984 | Cirincione ................. 73/863.32 |
| 4,519,258 A | | 5/1985 | Jakubowicz |
| 4,554,839 A | * | 11/1985 | Hewett et al. .............. 73/864.16 |
| 4,563,907 A | | 1/1986 | Johnson, Jr. et al. |
| 4,678,894 A | * | 7/1987 | Shafer ........................... 235/375 |
| 5,104,621 A | * | 4/1992 | Pfost et al. ....................... 422/67 |
| 5,133,218 A | | 7/1992 | Uffenhiemer et al. |
| 5,158,748 A | | 10/1992 | Obi et al. |
| 5,238,654 A | | 8/1993 | Nohl et al. |
| 5,401,253 A | | 3/1995 | Reynolds |
| 5,452,619 A | * | 9/1995 | Kawanabe et al. ........ 73/864.01 |
| 5,505,097 A | * | 4/1996 | Suovaniemi et al. ...... 73/864.18 |
| 5,567,122 A | | 10/1996 | Schulte |
| 5,743,886 A | | 4/1998 | Lynn et al. |
| 5,776,414 A | | 7/1998 | Itani et al. |
| 5,935,859 A | * | 8/1999 | Elliott et al. ..................... 506/33 |
| 5,983,733 A | * | 11/1999 | Strandberg et al. ........ 73/864.11 |
| 6,019,004 A | * | 2/2000 | Conley et al. .............. 73/864.16 |
| 6,060,022 A | | 5/2000 | Pang et al. |
| 6,116,099 A | * | 9/2000 | Carl ............................ 73/864.14 |
| 6,143,573 A | | 11/2000 | Rao et al. |
| 6,146,594 A | | 11/2000 | De Graaff et al. |
| 6,171,555 B1 | * | 1/2001 | Cargill et al. .................. 422/104 |
| 6,241,950 B1 | | 6/2001 | Veelenturf et al. |
| 6,343,717 B1 | | 2/2002 | Zhang et al. |
| 6,374,683 B1 | * | 4/2002 | Hunicke-Smith et al. . 73/864.17 |
| 6,387,330 B1 | * | 5/2002 | Bova et al. .................... 422/100 |
| 6,401,769 B1 | | 6/2002 | Backes et al. |
| 6,417,008 B2 | * | 7/2002 | Tyberg et al. ................. 436/180 |
| 6,495,106 B1 | * | 12/2002 | Kalra et al. .................... 422/100 |
| 6,551,557 B1 | | 4/2003 | Rose et al. |
| 6,656,724 B1 | * | 12/2003 | Heimberg et al. ......... 435/286.4 |
| 6,662,626 B2 | | 12/2003 | van der Maas |
| 6,814,936 B1 | * | 11/2004 | Enhorning .................... 422/100 |
| 6,968,749 B2 | * | 11/2005 | Chen et al. ................. 73/863.32 |
| 7,146,867 B2 | * | 12/2006 | Jagdhuber .................. 73/863.32 |
| 7,314,598 B2 | * | 1/2008 | Nishino ......................... 422/100 |
| 7,411,508 B2 | * | 8/2008 | Harazin et al. .............. 340/572.7 |
| 7,628,960 B2 | * | 12/2009 | Ruddock ....................... 422/100 |
| 2001/0005489 A1 | * | 6/2001 | Roach et al. .................... 422/99 |
| 2001/0034064 A1 | * | 10/2001 | Turner et al. ..................... 436/34 |
| 2002/0076351 A1 | | 6/2002 | Wernz et al. |
| 2002/0131903 A1 | * | 9/2002 | Ingenhoven et al. .......... 422/100 |
| 2003/0062265 A1 | * | 4/2003 | King et al. ..................... 204/453 |
| 2003/0155034 A1 | * | 8/2003 | De Beukeleer et al. ...... 141/130 |
| 2004/0022688 A1 | * | 2/2004 | Blackwood ................... 422/100 |
| 2004/0024364 A1 | | 2/2004 | Langley et al. |
| 2004/0033554 A1 | * | 2/2004 | Powers ........................... 435/29 |
| 2005/0058577 A1 | * | 3/2005 | Micklash et al. .............. 422/99 |
| 2005/0155438 A1 | | 7/2005 | Belgardt |
| 2006/0099115 A1 | * | 5/2006 | Sandberg ...................... 422/100 |
| 2007/0128084 A1 | * | 6/2007 | Coassin et al. ............... 422/100 |
| 2008/0019878 A1 | * | 1/2008 | Trump .......................... 422/100 |

FOREIGN PATENT DOCUMENTS

| | | |
|---|---|---|
| DE | 102 57 414 | 6/2004 |
| EP | 0 469 444 | 6/1997 |
| EP | 0 801 309 | 10/1997 |
| EP | 1 559 480 | 8/2005 |
| WO | 02/085521 | 10/2002 |
| WO | 2004/099059 | 11/2004 |
| WO | 2005/039771 | 5/2005 |
| WO | 2006/128662 | 12/2006 |

OTHER PUBLICATIONS

CTC Analytics AG, Front End Automation Systems for Liquid Chromatography, 6 pages.

Perkin Elmer Instruments, Series 200 Autosampler New Standard in automated sample processing, 2001, 8 pages.

Ring-Ling Chien et al., Parallel High Performance Liquid Chromatography, 1 page.

Shimadzu Corporation, Prominence Shimadzu High Performance Liquid Chromatograph, 3 pages.

Shimadzu Corporation, High throughput LC injection system, 2 pages.

Shimadzu Corporation, Autosampler for Shimadzu VP series HPLC System, 2 pages.

Thermo Electron Corporation, TriPlus Autosampler Flexible Sampling Solutions, 2004, 2 pages.

Waters, Waters 2777 Sample Manager, Installation and Maintenance Guide, 136 pages.

* cited by examiner

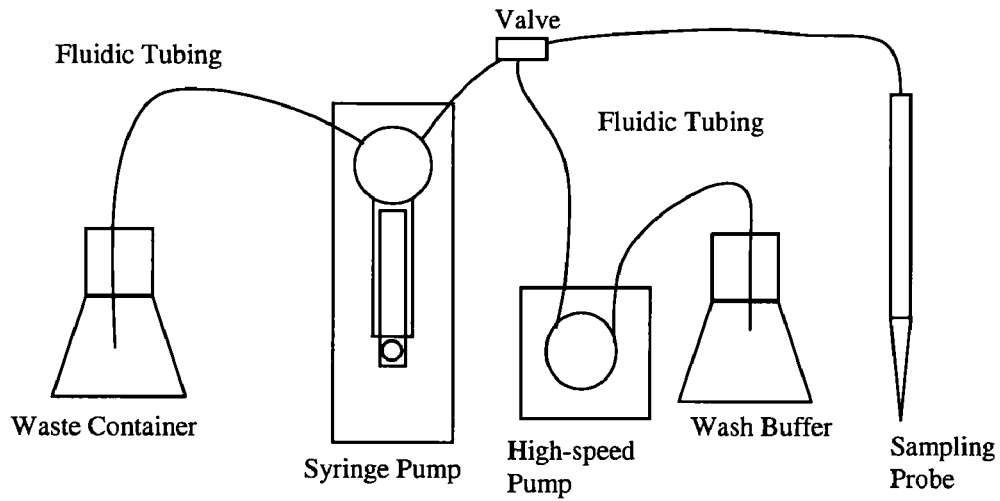
FIG. 1. Probe remote to metering device PRIOR ART
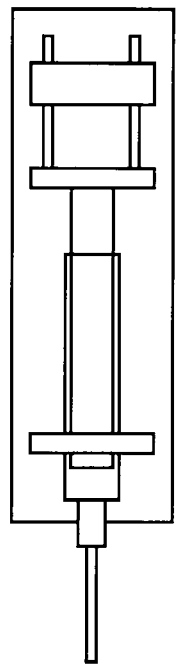
FIG. 2. Integrated probe and metering devices PRIOR ART

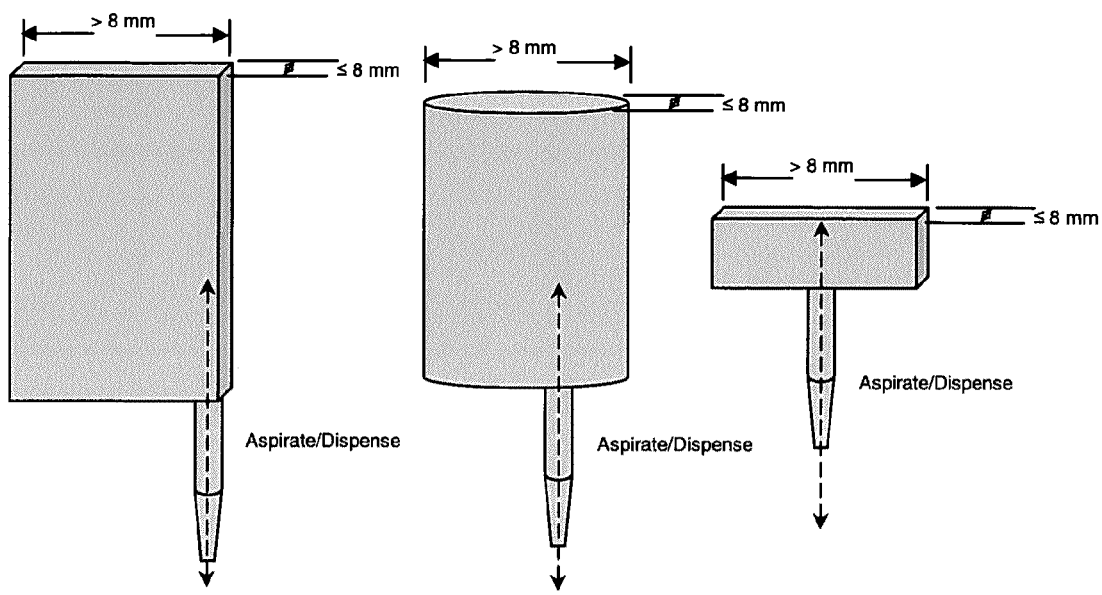
FIG. 8. Possible syringe probe shapes where only one dimension coincident with the aspirate/dispense axis is ≤ 8 mm.

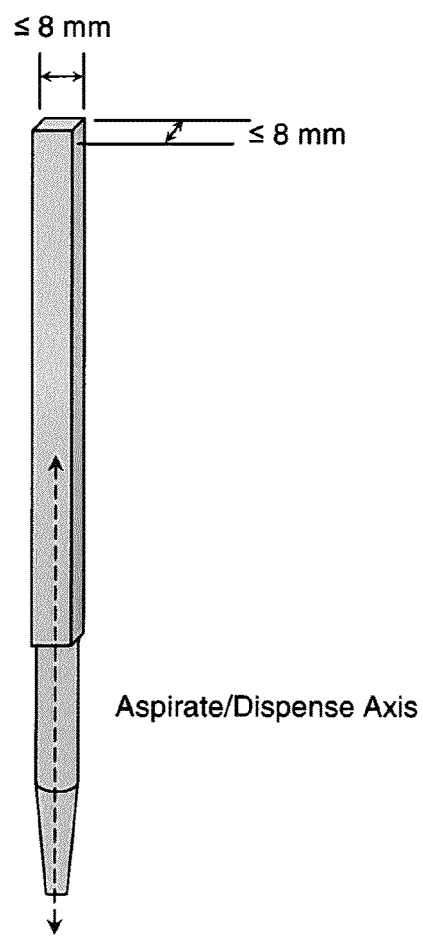
FIG. 9. Possible syringe probe shape where multiple, but not all, dimensions coincident with the aspirate/dispense axis are ≤ 8 mm.

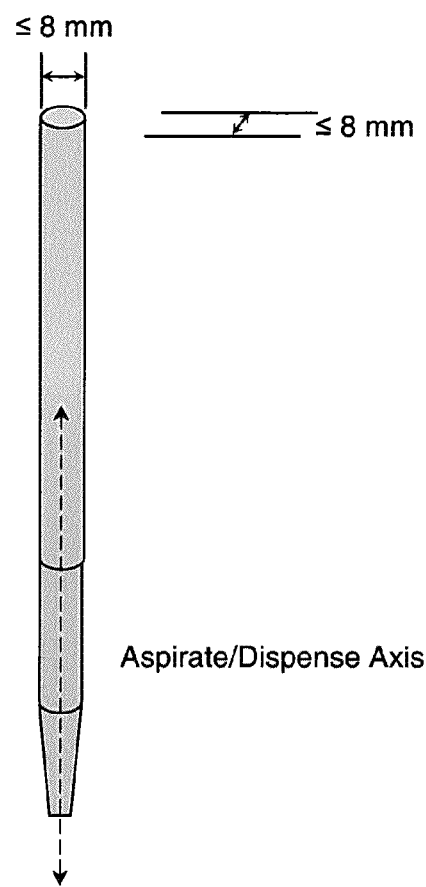
FIG. 10. Possible syringe probe shape where all dimensions coincident with the aspirate/dispense axis are ≤ 8 mm.

SAMPLING PROBE, GRIPPER AND INTERFACE FOR LABORATORY SAMPLE MANAGEMENT SYSTEMS

RELATED APPLICATIONS

This application is a continuation-in-part of U.S. Non-Provisional patent application Ser. No. 11/814,987 now U.S. Pat. No. 8,057,756, which was the National Stage of International Application No. PCT/US06/02845, filed Jan. 27, 2006. This application also claims the benefit of U.S. Provisional Application No. 61/015,487 filed Dec. 20, 2007. The referenced applications are each hereby incorporated by reference in their entireties.

FIELD OF THE INVENTION

The invention herein described relates generally to laboratory sample management operations and systems including robotic handling systems, components and methods, particularly for analytical applications, more particularly for liquid sample analytical systems, and still more particularly for bioanalytical and pharmaceutical applications.

BACKGROUND

Sample handling robots of various configurations are known in the biotechnology industry. A common feature of such systems is the use of a robotic or other motion control device to either move a fluid aspirating/dispensing syringe (herein generally referred to as a sampling probe) about a deck of vessels or other deck components like wash stations, reagent troughs, injection valves, etc., or to move the vessels and/or other deck components relative to a stationary sampling probe. Among the more sophisticated systems, plural sampling probes are ganged together for common movement by a sample handler.

There are two major types of fluidic sampling device designs used on automated liquid handling platforms for metering hundreds of nanoliters to milliliter volumes of liquid samples, reagents, diluents, etc in today's life science industry. Each design type possesses positive and negative attributes that must be weighed against each other when deciding which is better for a particular application.

The first type of design for automated fluidic metering uses a sampling probe remote to the metering device (commonly a stepper driven syringe). A fluidic tube, long enough to permit the probe to freely reach an ensemble of vessels on a robotic deck, is required to connect the probe to the metering device (see FIG. 1). For automated operation, the probe is attached to an X, Y, and Z motion mechanism while the relatively large and heavy metering device remains stationary and fixed to the automation device. In many implementations, a high-speed pumping device is valved between the metering device and probe. This pump is used to quickly wash the probe between uses in order to reduce contamination and carryover.

The most notable disadvantage of this design is that the relatively large fluid volume between the metering device and sampling probe acts as a "fluidic capacitor" causing imprecision in volumetric metering especially when aspirating and dispensing fluids against medium to high pressures. For conventional syringe pumps and tubing volumes used in today's robotic systems, the volumetric uncertainty is in the tens of microliters to hundreds of nanoliters range. This is tolerable when handling volumes in the hundreds of microliters and larger. It is not acceptable for smaller volumes, however as many of today's high-throughput, high technology applications operate in the sub hundred-microliter regime.

The second type of design for automated fluidic metering uses an integrated sampling probe and metering device (see FIG. 2). This overcomes the "fluidic capacitance" problem resulting from the requisite liquid volumes involved with the remote metering/sampling devices described above. Designs of this type are generally capable of delivering against approximately 150 psi.

The disadvantages with this approach are: 1) It is difficult to make the probe small enough to achieve the 9 mm center-to-center spacing preferred by today's high throughput applications; 2) The integrated metering and sampling device has more mass for the gantry to move around resulting in potential speed, accuracy, and precision compromises in the gantry's motion. This is generally overcome by using more robust and higher quality motion equipment, which, unfortunately, also has a commensurate increase in cost; 3) An electrical connection is required to power to the device; and 4) devices having barrel portions small enough to be on 9 mm centers to create an array of fluidic channels connect all the channels to a single platen causing every channel in the array to aspirate and/or dispense the same volume. This is very often an undesirable constraint.

SUMMARY OF THE INVENTION

At least one embodiment of the invention provides a sampling system comprising: a plurality of sampling probes, each sampling probe comprising a drive module and a syringe module removably coupled coaxially to the drive module to allow for different syringe modules to be interchangeably coupled to the drive module, each probe having a dimension that is 9 mm or less in at least one projection coincident with an aspirate/dispense axis of the probe; and a carrier for carrying the plurality of sampling probes wherein the probes are oriented to be 9 mm or less between adjacent aspirate/dispense axes of the plurality of probes.

At least one embodiment of the invention provides a sampling probe including a barrel, a plunger movable in the barrel for dispensing and/or aspirating a material, and an electronically readable identifier, the probe having a dimension that is 8 mm or less in at least one projection coincident with an aspirate/dispense axis of the probe.

At least one embodiment of the invention provides a sampling probe comprising: a drive module; a syringe module, the syringe module removably coupled coaxially to the drive module to form the sampling probe, wherein the sampling probe has a dimension that is 8 mm or less in at least one projection coincident with an aspirate/dispense axis of the sampling probe; a memory for onboard storage of audit information and/or operational instruction sets, and a communication device for effecting transfer of such audit information and/or operational instruction sets to and/or from an external device.

BRIEF DESCRIPTION OF THE DRAWINGS

Embodiments of this invention will now be described in further detail with reference to the accompanying drawing, in which:

FIG. 1 is a schematic of a prior art sampling system having the probe remote to the metering device;

FIG. 2 is a schematic of a prior art probe having an integral metering device;

FIG. 8 shows perspective views of probe assembly shapes wherein the probe is 8 mm or less in only one projection coincident with the aspirate/dispense axis;

FIG. 9 shows a perspective view of a probe assembly shape wherein the probe is 8 mm or less in only two projections coincident with the aspirate/dispense axis; and FIG. 10 shows a perspective view of a probe assembly shape wherein the probe is 8 mm or less in all projections coincident with the aspirate/dispense axis.

DETAILED DESCRIPTION OF THE DRAWINGS

Figure 3:
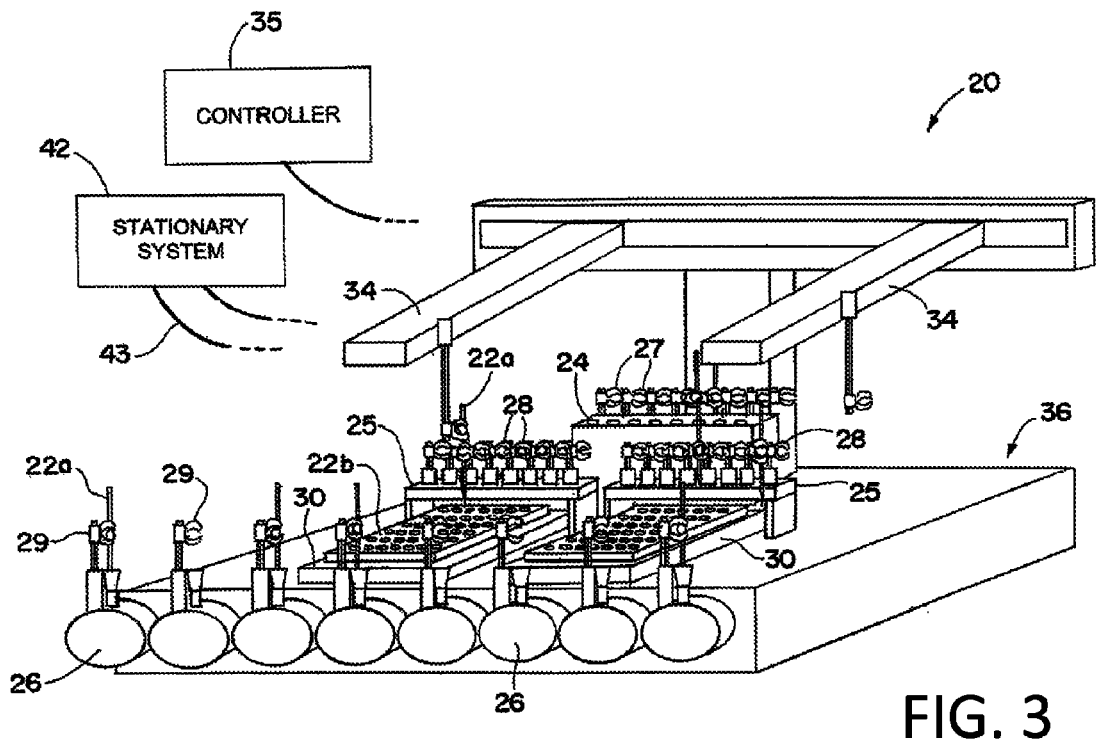
FIG. 3 is a schematic illustration of an exemplary embodiment of an analytical system.

Because the invention was conceived and developed for use in an adaptive, synchronized motion and fluids system for automating the sample handling process associated with analytical processes and especially bioanalytical processes such as introducing samples into LC systems, HPLC systems, etc., it will be herein described chiefly in this context. However, the principles of the invention in their broader aspects can be adapted to other types of systems. Referring now in detail to the drawings and initially to FIG. 3, an exemplary embodiment of an analytical system is generally denoted by reference numeral 20. The system 20 comprises one or more movable devices 22 for use in the performance of one or more analytical operations, which movable devices may be active devices, such as sampling probes 22a, and/or passive devices, such as trays 22b. The system further comprises one or more stations which, as shown, may be arranged in groups. For example, the system 20 includes one or more wash stations 24, one or more aspirating stations 25 (two shown), and one or more analysis stations 26. The stations 24, 25 and 26 have respectively associated therewith one or more receivers 27, 28 and 29 for receiving one or more of the movable devices 22a so that a prescribed operation can be commenced at the respective station. The stations 25 also are provided with a receiver 30 for the trays 22b. The system further comprises one or more transport mechanisms 34 for transporting the movable devices 22 from station to station, and a controller 35 for directing the transport mechanism to leave at least one of the movable devices with the receiver(s) in a first one of the stations thereby to free the transport mechanism for transport of at least one other movable device between stations while the movable device or devices left at the first station are used to perform a prescribed operation at the first station. Simply, the moveable devices are transported to and among receivers via the transport mechanism. Once transported, the moveable devices are "released" to the receivers by the transport mechanism, thereby freeing the transport mechanism for transporting other moveable devices between the stations.

In the illustrated embodiment, the stations are arranged in relation to what is commonly referred to a "deck" 36. As a result of the foregoing arrangement, many operations can be executed in parallel, thereby increasing overall system efficiency and throughput relative to the prior art systems where the movable device remains attached to the transport mechanism for effecting an operation. The movable devices 22, and particularly the active movable devices 22a, can be positioned anywhere in the system without constraint on other movable devices, active or passive. The transport mechanisms 34 can be, but are not limited to, robots, particularly robotic devices capable of three-dimensional translating (X, Y and Z axis) and/or rotational movement; levitation devices; antigravity devices; automated slides or tracks; stackers; and human beings. The transport mechanisms can be equipped with a suitable holder for the movable device being transported. As will be appreciated, multiple transport mechanisms may be employed and independently operated to retrieve and transport the movable devices. In addition, the movable devices may be transported by attending personnel, as in response to instructions provided by controller either audibly, visually and/or otherwise.

The movable devices 22 can be, but are not limited to, sampling probes/syringes; reaction vessels; plate carriers; sample loops; and other active or passive devices. An active movable device is one that is capable of performing an action, such as a syringe that can aspirate or dispense an agent. A passive movable device is one that does not perform an action but which can receive or be subjected to an action, such as a vial containing a sample or a tray containing multiple samples.

Figure 4:
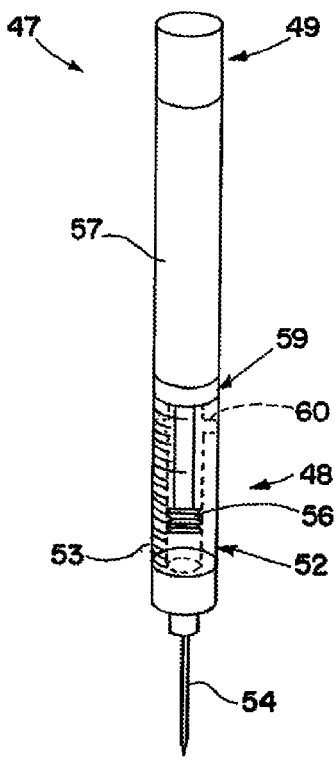
FIG. 4 is an illustration of an exemplary self-contained sampling probe useful in the analytical system of FIG. 3.

The movable devices 22 may include one or more sampling probes (e.g. syringes or pipettes) for aspirating and/or dispensing an agent. An exemplary untethered self-contained sampling probe is denoted by reference numeral 47 in FIG. 4. The probe 47 may include a dedicated metering device 48 for independent aspiration and/or dispensing of an agent, and control circuitry 49 for communicating with the overall system controller 35 (or components thereof) and for controlling the metering device. The metering device may include a syringe 52 including a syringe barrel 53 terminating at a lumen (e.g. needle) 54, a plunger 56 movable in the barrel for drawing and/or dispensing a fluid into and/or from the barrel via the lumen, and a motive device 57, such as an electric motor, for moving the plunger via an appropriate gear train or other transmission components. In addition, the sampling probe 47 may include a power supply 59 for powering the motor and associated control circuitry, or other means by which power is supplied to the syringe at a station. Command signals may be communicated wirelessly between the sampling probe and system controller (or components thereof), or by a make and break signal connection at point of placement (physical electrical contact or inductive), clip on control circuitry, and/or by other suitable means.

The probes may contain a time of day clock and may be used for timed reactions. For example, the probe may automatically draw up a plurality of solutions, mix them in its barrel, and hold them for a designated amount of time before expelling them. It may also automatically draw up a solution or solutions, wirelessly tell the controller 35 to inform the user to place the syringe in a laboratory device or container separate from its current location (e.g. incubator or refrigerator), sit in the device or container for a designated amount of time, and wirelessly tell the controller to tell the user to remove it from the device or container so it can become part of the active system again. The syringe barrel may also have a cross-port 60 allowing for fast washing once the plunger is fully retracted.

According to one embodiment, the controller (or dedicated components thereof such as a transport controller) need not know a priori or deterministically which movable devices will require transport at any given time. Instead, the movable devices can be configured to request service at the appropriate point within their current workflow and the transport mechanism commanded in response to that request. As may be desired, each movable device may be uniquely identifiable within its control logic to allow control transmissions to reach a specific device on a "hub" via a "broadcast" transmission scheme.

Figure 5:
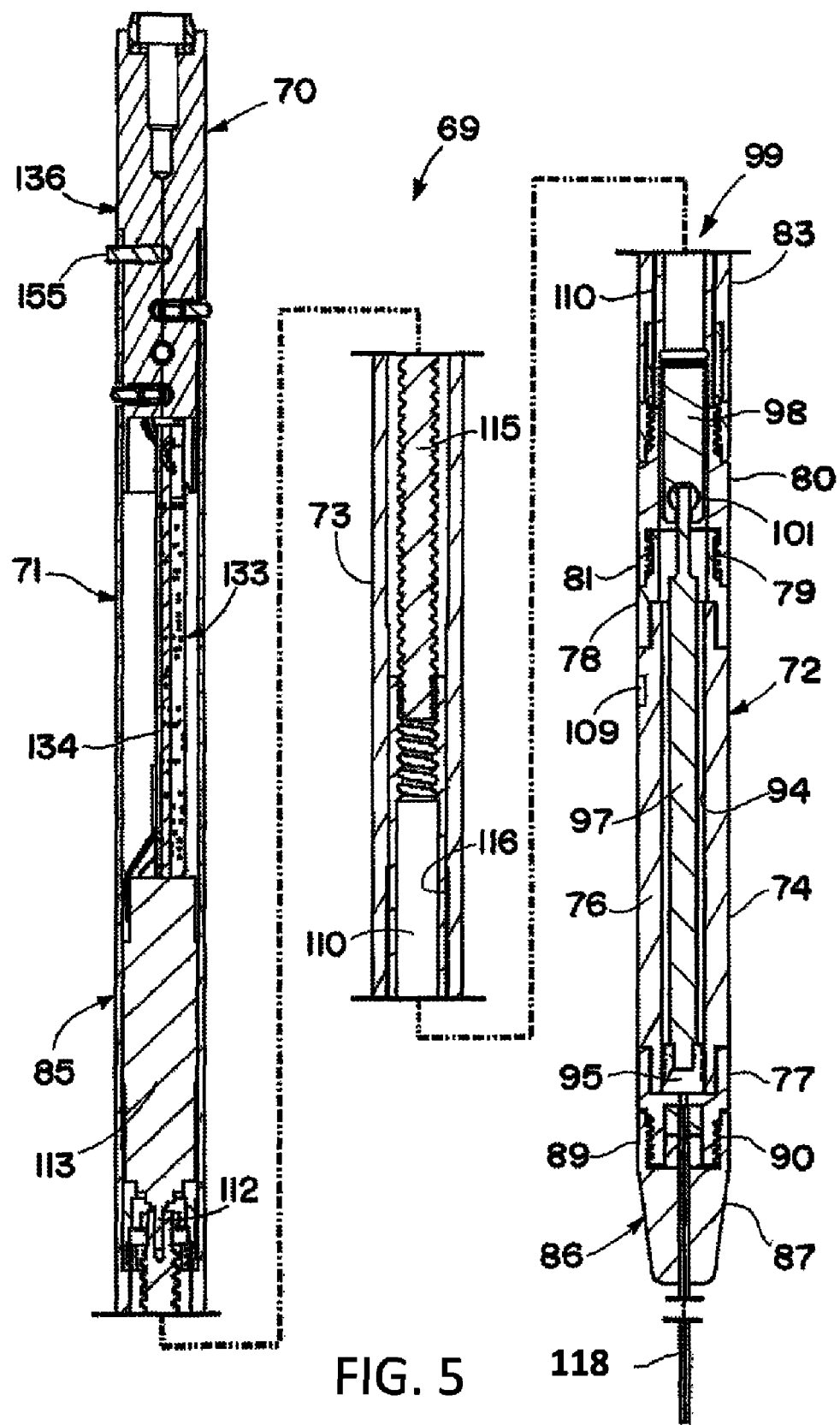
FIG. 5 is a cross-sectional view of an exemplary sampling probe according to the present invention, which probe comprises connector, drive and syringe modules.

Referring now to FIG. 5, an exemplary self-contained sampling probe according to the present invention is indicated generally by reference numeral 69. The sampling probe generally comprises a connector module 70, a drive module 71 and a syringe module 72 removably coupled coaxially to the drive module to allow for different syringe modules to be interchangeably coupled to the drive module. This allows, for example, replacement of second syringe modules including barrels having different capacities or to replace broken or leaking barrels.

The probe modules 70-72 may be interconnected by any suitable means that preferably allows for quick and easy replacement of one module for another. In the illustrated sampling probe, the drive and syringe modules are removably coupled by mating threads, thereby permitting the syringe module to be screwed onto and off of the drive module. The connector and drive modules are removably coupled by a sleeve and pin connection. Although screw and sleeve/pin connections are shown, other types of connections may be used to removably interconnect the drive and syringe module housings, such as quarter turn locking connections, ball and socket connections (like those to hold sockets onto ratchets), "U" nuts, wedge pins, Swage connections, or set screws.

More particularly, the drive module 71 and syringe module 72 respectively include a drive module housing 73 and a syringe module housing 74, each forming an axial continuation of the other. The syringe module housing includes a transparent or translucent plunger barrel 76, an outer end piece 77 at the axially outer end of the barrel, and an inner end piece 78 at the axially inner end of the barrel. The inner end piece 78 has a reduced diameter, externally threaded end portion 79 that is threaded into a counterbored, internally threaded axially inner end portion 81 of an end sleeve member 80 used to connect to the end of the drive module housing 73. The end sleeve member 80 is screw-connected to a main tubular body portion 83 of the drive module housing 73.

The module housings 71 and 72 are shown cylindrical with the outer surfaces thereof having for the most part the same outer diameter such that together the housings form a probe housing 85 having a substantially continuous cylindrical outer surface of uniform diameter. In one embodiment, the maximum outer diameter of the probe housing 75 is equal or less than 8 mm so that the sampling probes can be ganged together or individually placed next to each other dynamically during operation as in a grid pattern at a 9 mm center-to-center spacing, or less.

The outer end piece 77 of the syringe module housing 72 has fastened thereto a needle assembly 86 including a needle support body 87 that supports a needle 118 (e.g. any suitable lumen). The needle support body 87, which may be tapered as shown in FIG. 3, has an internally threaded inner end portion 89 screwed onto a reduced diameter, externally threaded end portion 90 of the outer barrel end piece 77. The taper serves as a lead-in to the receiving elements during placement of the syringe as well as helping to reduce the chance of scoring or shearing the sealing material present in some of the receiving elements. The screw-on connection means (or other suitable means) allows for easy interchange of different needle assemblies as needed. It also allows for connection of other elements such as valves to allow the syringe to be used as a syringe pump. The needle assemblies may have different length and/or diameter needles for different applications, as well as different types of needles. The needle support body 87 includes a central passage for the needle 118 that protrudes from the outer end of the needle support body. The inner end of the needle, which may be provided with a larger diameter collar, may be secured within a recess in the end portion 90 of the outer barrel end piece 77 by the needle support body. The inner end of the needle may be sealed by a Teflon face seal to the bottom wall of the recess that includes a center passage providing for fluid communication between the end of the needle and the interior of the barrel 76. The barrel 76 has a cylindrical interior chamber 94 in which a plunger 95 moves axially for dispensing and/or aspirating a fluid from and/or into the chamber 94. The plunger and barrel may be of a conventional construction that provides for a fluid tight seal between the plunger and barrel while allowing axial movement of the plunger in the barrel. The plunger 95 is connected to the end of a plunger rod 97 that connects the plunger to an axially movable drive coupling 98 of a plunger drive assembly 99 included in the drive module 71. While any suitable type of connection may be used, preferably a ball and socket connection is provided to accommodate any misalignment between the plunger rod and an axially driven coupling of the drive assembly. More particularly, the joint may be a miniature universal joint that ensures freedom of limited angular movement while maintaining axial stiffness with no relative axial motion. Also, a quick connect/disconnect connection is provided between the plunger rod and drive coupling to facilitate quick and easy connection and disconnection of the syringe module and drive module.

In the illustrated embodiment and as shown in FIG. 5, the coupling between the plunger rod 97 and drive coupling 98 is effected by an enlarged head 101 at the end of a reduced width/diameter neck or stem 102 at the inner end of the plunger rod and a socket 103 in the drive coupling 98. The head 101 shown is ball-shape and sized for a close fit within the socket, so that there is essentially no axial play between the plunger rod and drive coupling, while still allowing limited angular movement of the plunger rod relative to the drive coupling. A keyhole slot is provided in the side of the drive coupling 98 to allow the ball and stem to be inserted laterally into the drive coupling for seating of the ball 101 in the socket.

To connect the plunger rod 97 to the drive coupling 98, the plunger rod may be partially withdrawn from the syringe module housing 74 to allow the plunger rod to be grasped and manipulated. The ball 101 may then be inserted through the keyhole slot to connect the plunger rod to the drive coupling. Once connected, the housing of the syringe module may be screwed onto the housing of the drive module.

In view of the foregoing, the sampling probe 69 can be easily reconfigured by simply unscrewing a first syringe module including a plunger barrel from a drive module, and screwing onto the drive module a second syringe module. Typically the plunger will be provided in the syringe modules for replacement along with the syringe barrels.

As shown in FIG. 5, the drive coupling 98 in the illustrated embodiment is attached to (but may be formed integrally with) the nut 110 of a lead screw and nut assembly that is used to convert rotary motion of an output shaft 112 of a drive motor assembly 113 to linear motion of the nut. As shown, the nut 110 is a tubular member that is internally threaded to receive an externally threaded end of the drive coupling 98 which extends coaxially from the end of the nut. The nut also is internally threaded for driving engagement with a rotatable lead screw 115. As will be appreciated, rotation of the screw in one direction will move the nut axially in one direction and rotation of the screw in the opposite direction will move the nut axially in the opposite direction. The nut is guided for such linear axial movement in a guide passage 116 in the drive module housing 73. Although other types of anti-rotation devices may be used, in the illustrated embodiment the nut and guide passage have corresponding non-circular cross-sections for preventing rotation of the nut relative to the housing while permitting axial movement of the nut in the center bore of the housing.

As further depicted in FIG. 5, the syringe module 72 may be provided with an electronically readable identifier 109, such as a bar code or RFID device. The electronically readable identifier may be configured to store, for example, at least one of barrel volume information, date of manufacture, manufacturer certification, serialization information, location of manufacture, and specific calibration information as needed. The RFID or other identifier device may be located in or on the syringe module at any suitable location. Although an RFID device is shown seated in a recess in the side wall of the barrel, the RFID device, by way of further example, may be located in or on the sleeve 80 which may be made of a plastic material so as not to interfere with the function of the RFID device, whereas the barrel end pieces may be made of metal, such as stainless steel. The barrel will typically be made of glass or a plastic material that preferably is transparent or translucent. The syringe module may also include a memory for onboard storage of audit information and/or operational instruction sets, and a communication device for effecting transfer of such audit information and/or operational instruction sets to and/or from an external device.

Figure 6A:
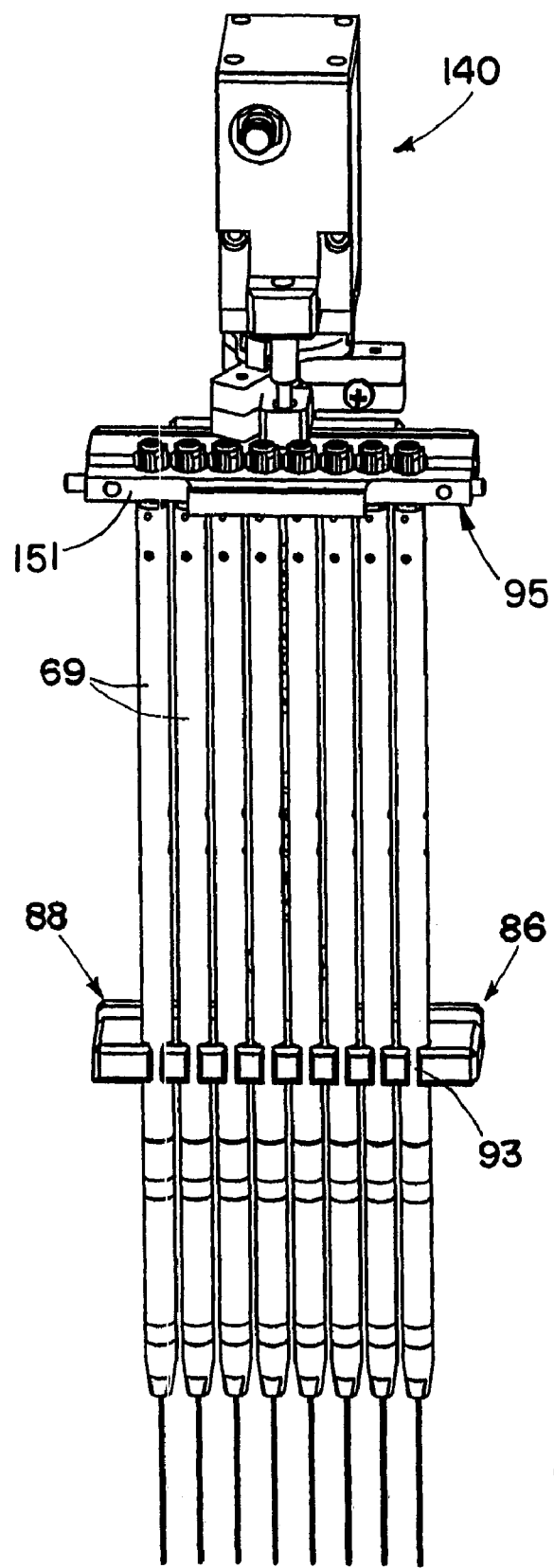
FIG. 6A is a front view of a gang of syringes contained in a carrier with a 9 mm center spacing in this example.
Figure 6B:
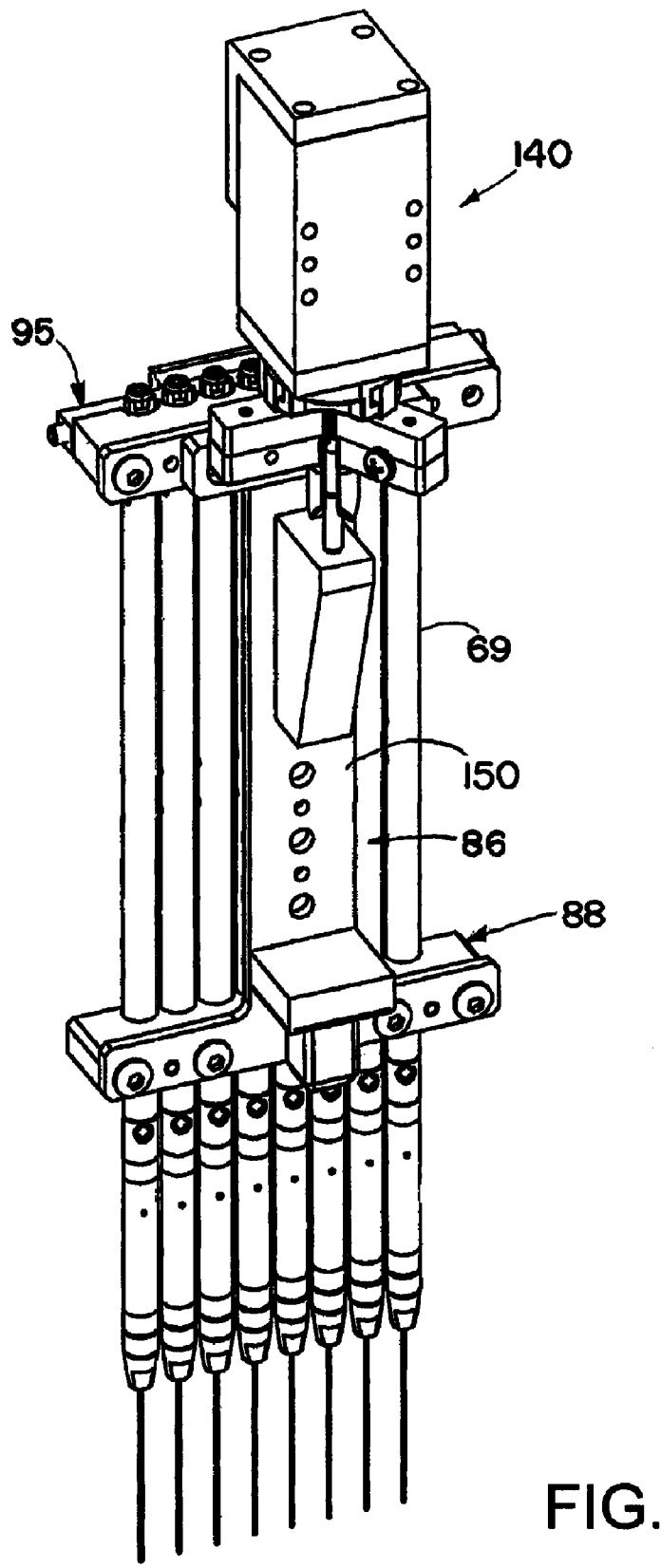
FIG. 6B is a back view of the ganged syringes of FIG. 6A.

Referring now to FIG. 6, a plurality of sampling probes 69 may be ganged together. In the illustrated embodiment, a gang of eight probes are contained in a carrier (holder) 86 with a 9 mm center to center spacing, although it will be appreciated that the spacing can be more or less and the number of probes can be varied as desired. A 9 mm center to center spacing is particularly desirable since it corresponds to conventional spacing used in 96 position racks/trays. The ganged probes function as an eight channel device for high throughput. That is, eight samples at a time, for example, can be transferred directly from a microwell plate with 9 mm spacing between wells to a 96 position or other device. As indicated, the number of ganged probes can be varied. By way of further example, the carrier could contain 96 probes arranged for example in an 8×12 array to provide 96 channels. Although carriers of various configurations could be used, the illustrated carrier 86 comprises a frame 88 including a central post 150 that interconnects upper and lower bars or racks 88 and 95. The racks have respective rows of slots 93 wherein the slots in each row are vertically aligned with respective slots in the other rack. The sampling probes are laterally supported in the slots against any significant lateral movement. In addition, the sampling probes are held against any significant vertical movement by a retention bar 151 attached to the upper rack (or by any other suitable means). The retention bar can be released to allow insertion of the probes into the racks and then closed to grip and thus hold the upper ends of the probes to the upper rack against vertical movement. The upper rack and retention bar have associated therewith contacts for engaging the probe contacts to effect electrical connection and/or communication between the probes and carrier.

The carrier 86 enables the gang of probes to be moved as a unit, such as by a gripper 140. The carrier includes a gripper post having a configuration similar to that of the gripper portion of the connector module of a probe. That is, the post includes grooves in which the fingers of the gripper can engage and the grooves may have associated therewith contacts that are engaged by the contacts of the gripper when the post is gripped by the gripper. The gripper post may be provided on a lug projecting from the backside of the carrier.

The contacts of the gripper post may be connected to the contacts that engage the contacts of the probes 69 when the latter are secured in the carrier, thereby enabling power, ground and/or communication to be supplied to probes during transport by the gripper. The gripper post contacts may also be connected to respective contacts provided in a plug on the carrier 86 that can plug into a socket of a grid module or other device to enable power, ground and/or communication to be supplied to the probes when the carrier is plugged into a grid module or other device and the gripper is released from the gang to perform other operations.

The carrier 86 may be plugged into (or formed integrally with) a hand-transportable element capable of programming each syringe in the carrier from a local interface or from a PC connection (wired or wireless) whereby each syringe in the collection may be instructed to perform parallel general laboratory operations such as aspirating, dispensing, aliquoting, dilution, reactions, being placed onto a sample injection device for sample introduction into LC or GC equipment, or other general laboratory operations. Sampling probes used in this manner can obviate transfers from container to container in as much as each probe serves as a container through several unit operations. In a practical sense, collections of probes can be handed from lab to lab or group to group for continued use throughout a sample's workflow. This has the benefit of reducing the number of surfaces with which the sample comes in contact and thus reduces sample loss commensurate with adsorption of sample molecule to such surfaces.

Figure 7A:
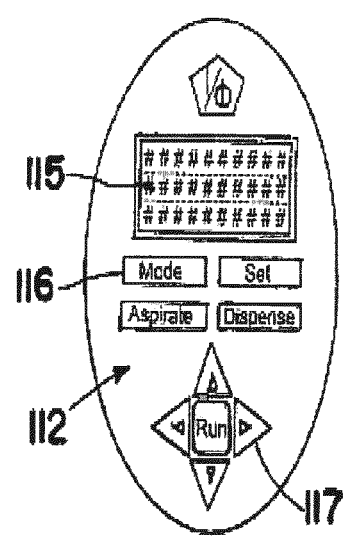
FIG. 7A is a plan view of a user interface employed in the hand-held device of FIG. 7.
Figure 7:
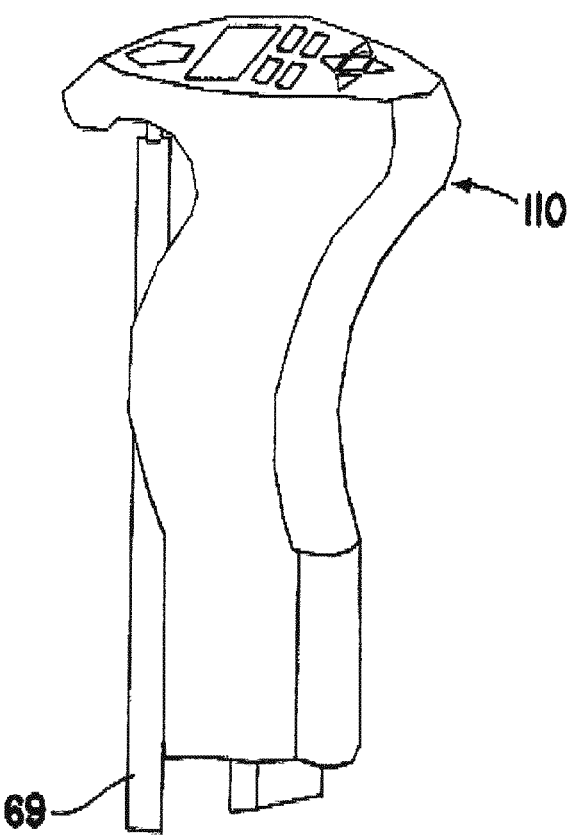
FIG. 7 is an illustration of a hand-held device to which a sampling probe is connected.

In FIG. 7, a hand-held carrier device 110 for a single sampling probe 69 is shown, but it will be appreciated the device can be configured to carry a plurality of sampling probes. The hand-held device may be tethered or untethered. If untethered, the device may carry its own power supply (e.g. battery) and may communicate wirelessly with the overall system controller. The hand-held device in either case may include it own processor and/or interface. An exemplary interface 112 is shown in FIG. 7A. As shown the interface 112 may include a display 115 and various user input devices such as buttons 116 and a navigating device 117. The processor and interface enable the probe and/or device to programmed to perform laboratory operations and or communicate with the technician that is carrying and/or manipulating the handheld device.

The form of the sampling probe 69 does not need to be 8 mm or less in all rotational dimensions about its aspirate/dispense axis as shown in FIGS. 3-6. The form of the sampling probe 69 may be 8 mm or less in at least one projection (face) about its aspirate/dispense axis. Several examples of syringe probe configurations fulfilling this requirement are illustrated in the FIGS. FIG. 8 illustrates exemplary shapes wherein only one projection coincident with the aspirate/dispense axis is ≦8 mm. FIG. 9 shows an example shape wherein two projections coincident with the aspirate/dispense axis are ≦8 mm. FIG. 10 shows an example shape wherein all projections coincident with the aspirate/dispense axis are ≦8 mm. It should be noted that many other shapes also fulfill the "at least one projection" criterion and the referenced FIGS. are meant solely to illustrate the requisite relationship between the projection(s) and the aspirate/dispense axis.

Although the invention has been shown and described with respect to a certain embodiment or embodiments, it is obvious that equivalent alterations and modifications will occur to others skilled in the art upon the reading and understanding of this specification and the annexed drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary embodiment or embodiments of the invention. In addition, while a particular feature of the invention may have been described above with respect to only one or more of several illustrated embodiments, such feature may be combined with one or more other features of the other embodiments, as may be desired and advantageous for any given or particular application.

What is claimed is:

1. A sampling system comprising:
a plurality of sampling probes, each sampling probe comprising a drive module and a syringe module removably coupled coaxially to the drive module to allow for different syringe modules to be interchangeably coupled to the drive module, each probe having an aspirate/dispense axis; and
a carrier for carrying the plurality of sampling probes;
wherein the probes have the aspirate/dispense axes thereof disposed at a spacing of 9 mm or less; and
wherein the carrier is a hand-held device to which the sampling probes are connected and electrically interfaced.

2. The sampling system of claim 1, wherein none of the plurality of sampling probes are tethered to a gantry of a robotic handling system.

3. The sampling system of claim 1, wherein at least one of the plurality of sampling probes is tethered to a gantry of a robotic handling system.

4. The sampling system of claim 1, wherein each probe includes an electronically readable identifier.

5. The sampling system of claim 4, wherein the electronically readable identifiers includes an RFID device.

6. The sampling system of claim 1, wherein each probe includes a memory for onboard storage of audit information and/or operational instruction sets, and a communication device for effecting transfer of such audit information and/or operational instruction sets to and/or from an external device.

7. The sampling system of claim 1, wherein each probe has at least two distinct dimensions that are 8 mm or less in at least one projection coincident with an aspirate/dispense axis of the probe.

8. The sampling system of claim 1, wherein each probe is 8 mm or less in all projections coincident with an aspirate/dispense axis of the probe.

* * * * *